United States Patent
Roomi et al.

(10) Patent No.: US 7,230,124 B2
(45) Date of Patent: Jun. 12, 2007

(54) ASCORBIC ACID COMPOUNDS, METHODS OF SYNTHESIS AND APPLICATION USE THEREOF

(75) Inventors: Waheed M. Roomi, Sunnyvale, CA (US); Shrirang Netke, Cupertino, CA (US); Vadim Ivanov, Castro Valley, CA (US); Aleksandra Niedzwiecki, San Jose, CA (US); Matthias Rath, 4699 Old Ironsides Rd. Suite 370, Santa Clara, CA (US) 95054

(73) Assignee: Matthias Rath, Heerlen (NL)

( * ) Notice: Subject to any disclaimer, the term of this patent is extended or adjusted under 35 U.S.C. 154(b) by 78 days.

(21) Appl. No.: 10/781,296

(22) Filed: Feb. 18, 2004

(65) Prior Publication Data

US 2004/0167077 A1    Aug. 26, 2004

(51) Int. Cl.
*C07D 307/62*    (2006.01)
(52) U.S. Cl. .................................... 549/315
(58) Field of Classification Search ............. 514/474; 549/315
See application file for complete search history.

(56) References Cited

U.S. PATENT DOCUMENTS

| | | |
|---|---|---|
| 5,536,500 A | 7/1996 | Galey |
| 5,607,968 A | 3/1997 | Ptchelintsev |
| 5,626,883 A | 5/1997 | Paul |
| 5,780,504 A | 7/1998 | Ptchelintsev |
| 5,801,192 A | 9/1998 | Dumas |
| 5,951,990 A | 9/1999 | Ptchelintsev |
| 6,162,419 A | 12/2000 | Perricone |

FOREIGN PATENT DOCUMENTS

| | | |
|---|---|---|
| EP | 0 891 771 | 1/1999 |
| JP | 63-19 0882 | 8/1988 |
| JP | 4-24 7011 | 9/1992 |
| JP | 6-78560 | 3/1994 |
| WO | WO 98/23152 | 6/1998 |

*Primary Examiner*—Taofiq Solola
(74) *Attorney, Agent, or Firm*—Inhouse Co.; Ali Kamarei, Esq.; Alexander Chen, Esq.

(57) ABSTRACT

A composition of L-ascorbic acid derivatives is described comprising L-ascorbic acid and lysine or lysine moieties, wherein L-ascorbic acid is covalently bound to the lysine or lysine moieties. The composition so described is used to prevent the degradation of extracellular matrix, stabilize connective tissue, is used to as an antioxident, and is used for treating damage to skin comprising applying the topical composition to the skin.

15 Claims, 4 Drawing Sheets

Structure of L-ascorbic acid

FIG. 1A

Structure of lysine

FIG. 1B

Structure of proline

FIG. 1C

Ascorbyl lysine

Ascorbyl proline

6-Deoxybromo ascorbate

6-Deoxyascorbate lysine

ASCORBIC ACID COMPOUNDS, METHODS OF SYNTHESIS AND APPLICATION USE THEREOF

CLAIM OF PRIORITY

Applicant hereby claims priority to U.S. Provisional Application No. 60/314,857, filed on Aug. 24, 2001. This invention was not made by an agency of the United States Government or under a contract with an agency of the United States Government.

FIELD OF INVENTION

The invention relates to the novel synthesis of ascorbic acid compounds with lysine and its derivatives and/or proline and its derivatives. The present invention provides pharmaceutically effective composition which comprises the ascorbic acid derivatives with lysine and proline. The present invention also includes methods of use in research fields including, but not limited to, medicine, nutrition, physiology, and pharmacology applications.

BACKGROUND OF INVENTION

L-Ascorbic acid, also known as vitamin C, is an important dietary factor. It is not synthesized in vivo in human, monkey and guinea pig and therefore is listed as an essential nutritive element. This ubiquitous compound is essential for the maintenance and preservation of several species including human being. Scurvy has been known as a condition due to deficiency of L-ascorbic acid and is marked by weakness of the skin, petechial hemorrhage, ecchymosis, and hemorrhages in the gingiva and marrow, which can be life threatening. To prevent scurvy for the maintenance of health, a recommended daily administration is established for L-ascorbic acid; in particular, 60 mg for adult male and 50 mg for adult female.

L-ascorbic acid is probably the most effective, efficient and least toxic antioxidant. It is a water soluble, chain-breaking antioxidant. The mechanism of action involves L-ascorbic acid acting as scavenger for harmful radicals like superoxide, hydroxyl and singlet oxygen that are produced during normal or pathological cellular metabolism. Ascorbic acid is speculated to be superior to other water soluble and lipid soluble antioxidants. It also protects DNA, enzyme, protein and lipids from oxidative damage and thereby prevents aging, coronary heart diseases, cataract formation, degenerative diseases and cancer. Oxygen radicals have been implicated not only in initiation and post-initiation stages of carcinogenesis, but also in invasion and metastatic processes.

L-Ascorbic acid takes part in several important physiological functions in vivo. It is essential for collagen synthesis, proteoglygans and various components of extra cellular matrix (ECM). It helps to maintain various enzymes in their reduced forms. L-Ascorbic acid is involved in the hydroxylation of lysine and proline to the formation of hydroxylysine and hydroxproline which are necessary for the synthesis of collagen in living connective tissues. These reactions are mediated by lysly hydroxylase and prolyl hydroxylase for which L-ascorbic acid functions as cofactor. Lysine and proline are principal components of tendons, ligaments, skin, bone, teeth, cartilage, heart valves, cornea, eye lens and ground substances between cells. Hydroxproline and hydroxlysine are required for the formation of a stable ECM and cross link in the fibers. Any deficiency of L-ascorbic acid reduces the activity of prolyl hydroxylase and lysyl hydroxylase. This results in impaired formation of collagen which leads to tissue weakness and eventually, scurvy.

Medicine considers L-ascorbic acid and lysine as one of the most important natural substances that is indispensable for maintenance of health at the cellular level. Deficiency of these substances in humans may lead to various diseases. Almost all diseases are a culmination of a lack of L-ascorbic acid and lysine. Lysine inhibits the destruction of collagen molecules by binding with plasminogen and thus preventing its breakdown to plasmin, which is one of the enzymes responsible for breakdown of collagen and for activating other matrix metallo proteinases (MMPs). Since our body cannot produce its own lysine, it has to be supplied through diet or from dietary supplements. Another important amino acid, Proline, is presumed to be synthesized in the body in adequate quantities for normal functions. It is likely that under stress conditions the quantity synthesized falls short of the body needs. This often leads to a conditioned deficiency of this important amino acid.

Another hydroxproline containing protein is the plasma complement component Clq, which constitutes an integral part of the protective mechanism against pathogens. The concentration of Clq is significantly reduced in guinea pigs fed a ascorbic acid deficient diet. In addition, L-ascorbic acid participates in the biosynthesis of carnitine and neuroendocrine peptides.

L-Ascorbic acid has several reactive hydroxy groups that can be used for the synthesis of a number of derivatives. Many substituted compounds at 2-, 3-, 5- and 6-positions have been synthesized. L-ascorbate 2-sulphate is stored in fish and some shrimp. It has the L-ascorbic acid activity for fish such as trout, salmon and catfish. It is 20 times more stable than ascorbic acid. Hence, it has been used in the formulation of feeds. L-ascorbate 2-phosphate is more stable in air than ascorbic acid. This compound is used as source of L-ascorbic acid in guinea pigs and rhesus monkeys. L-ascorbyl 6-palmitate, a synthetic lipophilic ascorbic acid derivative, is another effective preservative in foods and pharmaceuticals.

In recent years there has been a growing interest in the therapeutic application of L-ascorbic acid and its derivatives as an anti-cancer agent.

SUMMARY OF INVENTION

The invention relates to the novel synthesis of ascorbic acid compounds with lysine and its derivatives and/or proline and its derivatives. The present invention provides pharmaceutically effective composition which comprises the ascorbic acid derivatives with lysine and proline.

These new biochemical compounds can provide additional biological effects superior to its individual components. Thus a biochemical synthesis of these compounds in which the amino acids are covalently bound to ascorbic acid is preferable to a simple physical mixture of the amino acids with ascorbic acid.

Such unexpected superior biological effects include increased biological stability of these molecules, enhanced absorption by various biological cell compartments and greater biological efficacy. Such compounds can facilitate and enhance the assimilation of other nutritional components from foods resulting in improved nutritional status of individuals. These novel compounds have applications in a variety of areas including but not limited to nutrition, medicine and pharmacology.

The present invention also includes methods of use in research fields including, but not limited to, medicine, nutrition, physiology, and pharmacology applications.

The overall objective of this invention is to synthesize ascorbic acid derivatives with lysine and proline moieties. The synthesis will be carried out using L-ascorbic acid, L-lysine and L-proline. The standard procedure for the condensation of an alcohol with an acid to produce ester will be used. For this purpose, the —$CH_2OH$ of ascorbic acid at 6-position and the carboxyl group of either lysine or proline will be utilized. Several types of compounds using multiple lysine, multiple proline, or their combinations can be formed using this scheme. Some of the possible compounds that can be obtained through this procedure are shown.

BRIEF DESCRIPTION OF THE INVENTION

FIG. 3a also shows the scheme to synthesize 6-deoxyascorbate proline. This scheme utilizes the HN-of proline for binding with 6-deoxybromo ascorbate to produce derivatives linked at 6-position.

DETAILED DESCRIPTION OF THE INVENTION

The present invention provides a process for preparing L-ascorbic acid derivatives, which comprising the steps of:
1) treating L-ascorbic acid with lysine or lysine moieties wherein L-ascorbic acid is covalently bound to the lysine or lysine moieties; and
2) isolating the L-ascorbic acid derivatives.

The present invention provides a process for preparing L-ascorbic acid derivatives, which comprising the steps of:
1) treating L-ascorbic acid with lysine or lysine moieties wherein L-ascorbic acid is covalently bound to the lysine or lysine moieties; and
2) isolating the L-ascorbic acid derivatives;
wherein the L-ascorbic acid is covalently bound to the lysine or lysine moieties in C-6 position of the L-ascorbic acid.

The present invention provides a process for preparing L-ascorbic acid derivatives, which comprising the steps of:
1) treating L-ascorbic acid with lysine or lysine moieties wherein L-ascorbic acid is covalently bound to the lysine or lysine moieties; and
2) isolating the L-ascorbic acid derivatives;
wherein the L-ascorbic acid is covalently bound to the lysine or lysine moieties in C-2 position of the L-ascorbic acid.

The present invention provides a process for preparing L-ascorbic acid derivatives, which comprising the steps of:
1) treating L-ascorbic acid with lysine or lysine moieties wherein L-ascorbic acid is covalently bound to the lysine or lysine moieties; and
2) isolating the L-ascorbic acid derivatives;
wherein the L-ascorbic acid is covalently bound to one or more lysine in C-6 position of the L-ascorbic acid.

The present invention provides a process for preparing L-ascorbic acid derivatives, which comprising the steps of:
1) treating L-ascorbic acid with lysine or lysine moieties wherein L-ascorbic acid is covalently bound to the lysine or lysine moieties; and
2) isolating the L-ascorbic acid derivatives;
wherein the L-ascorbic acid is covalently bound to one or more lysine in C-2 position of the L-ascorbic acid.

The present invention provides a process for preparing L-ascorbic acid derivatives, which comprising the steps of:
1) treating L-ascorbic acid with lysine or lysine moieties wherein L-ascorbic acid is covalently bound to the lysine or lysine moieties; and
2) isolating the L-ascorbic acid derivatives;
wherein the L-ascorbic acid is covalently bound to a first lysine in C-6 position and a second lysine in C-2 position of the L-ascorbic acid.

The present invention provides a process for preparing L-ascorbic acid derivatives, which comprising the steps of:
1) treating L-ascorbic acid with lysine or lysine moieties wherein L-ascorbic acid is covalently bound to the lysine or lysine moieties; and
2) isolating the L-ascorbic acid derivatives;
wherein the L-ascorbic acid is covalently bound to two or more lysine in C-6 position and one lysine in C-2 position of the L-ascorbic acid.

The present invention provides a process for preparing L-ascorbic acid derivatives, which comprising the steps of:
1) treating L-ascorbic acid with lysine or lysine moieties wherein L-ascorbic acid is covalently bound to the lysine or lysine moieties; and
2) isolating the L-ascorbic acid derivatives;
wherein the L-ascorbic acid is covalently bound to one lysine in C-6 position and two or more lysine in C-2 position L-ascorbic acid.

The present invention provides a process for preparing L-ascorbic acid derivatives, which comprising the steps of:
1) treating L-ascorbic acid with lysine or lysine moieties wherein L-ascorbic acid is covalently bound to the lysine or lysine moieties; and
2) isolating the L-ascorbic acid derivatives;
wherein L-ascorbic acid is covalently bound to two or more lysine in C-6 position and two or more lysine in C-2 position of the L-ascorbic acid.

The present invention provides a process for preparing L-ascorbic acid derivatives, comprising the steps of:
1) treating L-ascorbic acid with proline or proline moieties wherein the proline or proline moieties are covalently bound to L-ascorbic acid; and
2) isolating the L-ascorbic acid derivatives.

The present invention provides a process for preparing L-ascorbic acid derivatives, comprising the steps of:
1) treating L-ascorbic acid with proline or proline moieties wherein the proline or proline moieties are covalently bound to L-ascorbic acid; and
2) isolating the L-ascorbic acid derivatives;
wherein the L-ascorbic acid is covalently bound to proline in C-6 position of the L-ascorbic acid.

The present invention provides a process for preparing L-ascorbic acid derivatives, comprising the steps of:
1) treating L-ascorbic acid with proline or proline moieties wherein the proline or proline moieties are covalently bound to L-ascorbic acid; and
2) isolating the L-ascorbic acid derivatives;
wherein the L-ascorbic acid is covalently bound to proline in, C-2 position of the L-ascorbic acid.

The present invention provides a process for preparing L-ascorbic acid derivatives, comprising the steps of:
1) treating L-ascorbic acid with proline or proline moieties wherein the proline or proline moieties are covalently bound to L-ascorbic acid; and
2) isolating the L-ascorbic acid derivatives;
wherein the L-ascorbic acid is covalently bound to two or more proline in C-6 position of the L-ascorbic acid.

The present invention provides a process for preparing L-ascorbic acid derivatives, comprising the steps of:
1) treating L-ascorbic acid with proline or proline moieties wherein the proline or proline moieties are covalently bound to L-ascorbic acid; and
2) isolating the L-ascorbic acid derivatives;
wherein the L-ascorbic acid is covalently bound to two or more proline in C-2 position of the L-ascorbic acid.

The present invention provides a process for preparing L-ascorbic acid derivatives, comprising the steps of:
1) treating L-ascorbic acid with proline or proline moieties wherein the proline or proline moieties are covalently bound to L-ascorbic acid; and
2) isolating the L-ascorbic acid derivatives;
wherein the L-ascorbic acid is covalently bound to a first proline in C-6 position of the L-ascorbic acid and a second proline in C-2 position of the L-ascorbic acid.

The present invention provides a process for preparing L-ascorbic acid derivatives, comprising the steps of:
1) treating L-ascorbic acid with proline or proline moieties wherein the proline or proline moieties are covalently bound to L-ascorbic acid; and
2) isolating the L-ascorbic acid derivatives;
wherein L-ascorbic acid is covalently bound to a proline in C-2 position of the L-ascorbic acid and a polyproline in C-6 position of the L-ascorbic acid.

The present invention provides a process for preparing L-ascorbic acid derivatives, comprising the steps of:
1) treating L-ascorbic acid with proline or proline moieties wherein the proline or proline moieties are covalently bound to L-ascorbic acid; and
2) isolating the L-ascorbic acid derivatives;
wherein the L-ascorbic acid is covalently bound to a polyproline in C-2 position of the L-ascorbic acid and a proline molecule in C-6 position of the L-ascorbic acid.

The present invention provides a process for preparing L-ascorbic acid derivatives, comprising the steps of:
1) treating L-ascorbic acid with proline or proline moieties wherein the proline or proline moieties are covalently bound to L-ascorbic acid; and
2) isolating the L-ascorbic acid derivatives;
wherein the L-ascorbic acid is covalently bound to a first polyproline at C-2 of the L-ascorbic acid and a second polyproline at C-6 position of the L-ascorbic acid.

The present invention provides a process for preparing L-ascorbic acid derivatives, comprising the steps of:
1) treating 6-deoxybromoascorbate with lysine or lysine moieties wherein L-ascorbic acid is covalently bound to the lysine or lysine moieties; and
2) isolating the L-ascorbic acid derivatives;
wherein the 6-deoxybromoascorbate is covalently bound to one lysine.

The present invention provides a process for preparing L-ascorbic acid derivatives, comprising the steps of:
1) treating 6-deoxybromoascorbate with lysine or lysine moieties wherein L-ascorbic acid is covalently bound to the lysine or lysine moieties; and
2) isolating the L-ascorbic acid derivatives;
wherein the 6-deoxybromoascorbate is reacted to the $\epsilon$-NH$_2$ group of lysine.

The present invention provides a process for preparing L-ascorbic acid derivatives, comprising the steps of:
1) treating 6-deoxybromoascorbate with lysine or lysine moieties wherein L-ascorbic acid is covalently bound to the lysine or lysine moieties; and
2) isolating the L-ascorbic acid derivatives;
wherein the 6-deoxybromoascorbate is covalently bound to a polylysine.

The present invention provides a process for preparing L-ascorbic acid derivatives, comprising the steps of:
1) treating 6-deoxybromoascorbate with lysine or lysine moieties wherein L-ascorbic acid is covalently bound to the lysine or lysine moieties; and
2) isolating the L-ascorbic acid derivatives;
wherein the 6-deoxybromoascorbate is reacted to the $\epsilon$-NH$_2$ group of polylysine.

The present invention provides a process of producing L-ascorbic acid derivatives, comprising the steps of:
1) treating 6-deoxybromoascorbate with proline or proline moieties wherein L-ascorbic acid is covalently bound to the proline or proline moieties; and
2) isolating said L-ascorbic acid derivatives.

The present invention provides a process of producing L-ascorbic acid derivatives, comprising the steps of:
1) treating 6-deoxybromoascorbate with proline or proline moieties wherein L-ascorbic acid is covalently bound to the proline or proline moieties; and
2) isolating said L-ascorbic acid derivatives;
wherein the 6-deoxybromoascorbate is covalently bound to polyproline.

The present invention provides a process of producing L-ascorbic acid derivatives, comprising the steps of:
1) treating 6-deoxybromoascorbate with proline or proline moieties wherein L-ascorbic acid is covalently bound to the proline or proline moieties; and
2) isolating said L-ascorbic acid-derivatives;
wherein the 6-deoxybromoascorbate is covalently bound to a first of proline at C-2 position of the L-ascorbic acid and a polylysine at C-6 position of the L-ascorbic acid.

The present invention provides a process of producing L-ascorbic acid derivatives, comprising the steps of:
1) treating 6-deoxybromoascorbate with lysine/lysine moieties and proline/proline moieties wherein L-ascorbic acid is covalently bound to the lysine/lysine moieties and proline/proline moieties; and
2) isolating said L-ascorbic acid derivatives.

The present invention provides a process of producing L-ascorbic acid derivatives, comprising the steps of:
1) treating 6-deoxybromoascorbate with lysine/lysine moieties and proline/proline moieties wherein L-ascorbic acid is covalently bound to the lysine/lysine moieties and proline/proline moieties; and
2) isolating said L-ascorbic acid derivatives;
wherein the 6-deoxybromoascorbate is covalently bound to a proline at C-2 position of the L-ascorbic acid and one lysine at C-6 position of the L-ascorbic acid.

The present invention provides a process of producing L-ascorbic acid derivatives, comprising the steps of:
1) treating 6-deoxybromoascorbate with lysine/lysine moieties and proline/proline moieties wherein L-ascorbic acid is covalently bound to the lysine/lysine moieties and proline/proline moieties; and
2) isolating said L-ascorbic acid derivatives;
wherein the 6-deoxybromoascorbate is covalently bound to a proline at C-6 position of the L-ascorbic acid and a polylysine at C-2 position of the L-ascorbic acid.

The present invention provides a process of producing L-ascorbic acid derivatives, comprising the steps of:
1) treating 6-deoxybromoascorbate with lysine/lysine moieties and proline/proline moieties wherein L-ascorbic acid is covalently bound to the lysine/lysine moieties and proline/proline moieties; and
2) isolating said L-ascorbic acid derivatives;
wherein the 6-deoxybromoascorbate is covalently bound to a polyproline at C-6 of the L-ascorbic acid and one lysine at C-2 of the L-ascorbic acid.

The present invention provides a process of producing L-ascorbic acid derivatives, comprising the steps of:
1) treating 6-deoxybromoascorbate with lysine/lysine moieties and proline/proline moieties wherein L-ascorbic acid is covalently bound to the lysine/lysine moieties and proline/proline moieties; and
2) isolating said L-ascorbic acid derivatives;
wherein the 6-deoxybromoascorbate is covalently bound to the $\epsilon$-NH$_2$ group of lysine.

The present invention provides a process of producing L-ascorbic acid derivatives, comprising the steps of:
1) treating 6-deoxybromoascorbate with lysine/lysine moieties and proline/proline moieties wherein L-ascorbic acid is covalently bound to the lysine/lysine moieties and proline/proline moieties; and
2) isolating said L-ascorbic acid derivatives;
wherein the 6-deoxybromoascorbate is covalently bound to a proline at C-6 position of the L-ascorbic acid and a polylysine at C-6 position of the L-ascorbic acid.

The present invention provides a process of producing L-ascorbic acid derivatives, comprising the steps of:
1) treating 6-deoxybromoascorbate with lysine/lysine moieties and proline/proline moieties wherein L-ascorbic acid is covalently bound to the lysine/lysine moieties and proline/proline moieties; and
2) isolating said L-ascorbic acid derivatives;
wherein the 6-deoxybromoascorbate is covalently bound to a proline and a lysine-proline at C-2 position of the L-ascorbic acid.

The present invention provides a process of producing L-ascorbic acid derivatives, comprising the steps of:
1) treating 6-deoxybromoascorbate with lysine/lysine moieties and proline/proline moieties wherein L-ascorbic acid is covalently bound to the lysine/lysine moieties and proline/proline moieties; and
2) isolating said L-ascorbic acid derivatives;
wherein the 6-deoxybromoascorbate is covalently bound to a proline and a proline-lysine at C-2 position of the L-ascorbic acid.

The present invention provides a process of producing L-ascorbic acid derivatives, comprising the steps of:
1) treating 6-deoxybromoascorbate with lysine/lysine moieties and proline/proline moieties wherein L-ascorbic acid is covalently bound to the lysine/lysine moieties and proline/proline moieties; and
2) isolating said L-ascorbic acid derivatives;
wherein the 6-deoxybromoascorbate is covalently bound to the $\epsilon$-NH$_2$ group of lysine.

The present invention provides a process of producing L-ascorbic acid derivatives, comprising the steps of:
1) treating 6-deoxybromoascorbate with lysine/lysine moieties and proline/proline, moieties wherein L-ascorbic acid is covalently bound to the lysine/lysine moieties and proline/proline moieties; and
2) isolating said L-ascorbic acid derivatives;
wherein the 6-deoxybromoascorbate is covalently bound to the $\alpha$-NH$_2$ group of polylysine.

The present invention provides a process of producing L-ascorbic acid derivatives, comprising the steps of:
1) treating 6-deoxybromoascorbate with lysine/lysine moieties and proline/proline moieties wherein L-ascorbic acid is covalently bound to the lysine/lysine moieties and proline/proline moieties; and
2) isolating said L-ascorbic acid derivatives;
wherein the 6-deoxybromoascorbate is covalently bound to lysine-proline.

The present invention provides a process of producing L-ascorbic acid derivatives, comprising the steps of:
1) treating 6-deoxybromoascorbate with lysine/lysine moieties and proline/proline moieties wherein L-ascorbic acid is covalently bound to the lysine/lysine moieties and proline/proline moieties; and
2) isolating said L-ascorbic acid derivatives;
wherein the 6-deoxybromoascorbate is covalently bound to the $\alpha$-NH$_2$ group of lysine at C-6 position of the L-ascorbic acid and one proline at C-2 position of the L-ascorbic acid.

The present invention provides a process of producing L-ascorbic acid derivatives, comprising the steps of:
1) treating 6-deoxybromoascorbate with lysine/lysine moieties and proline/proline moieties wherein L-ascorbic acid is covalently bound to the lysine/lysine moieties and proline/proline moieties; and
2) isolating said L-ascorbic acid derivatives;
wherein the 6-deoxybromoascorbate is covalently bound to the $\alpha$-NH$_2$ group of polylysine at C-6 position of the L-ascorbic acid and one proline at C-2 position of the L-ascorbic acid.

The present invention provides a process of producing L-ascorbic acid derivatives, comprising the steps of:
1) treating 6-deoxybromoascorbate with lysine/lysine moieties and proline/proline moieties wherein L-ascorbic acid is covalently bound to the lysine/lysine moieties and proline/proline moieties; and
2) isolating said L-ascorbic acid derivatives;
wherein the 6-deoxybromoascorbate is covalently bound to the $\alpha$-NH$_2$ group of lysine at C-6 position of the L-ascorbic acid and a polyproline at C-2 position of the L-ascorbic acid.

The present invention provides a process of producing L-ascorbic acid derivatives, comprising the steps of:
1) treating 6-deoxybromoascorbate with lysine/lysine moieties and proline/proline moieties wherein L-ascorbic acid is covalently bound to the lysine/lysine moieties and proline/proline moieties; and
2) isolating said L-ascorbic acid derivatives;
wherein the 6-deoxybromoascorbate is covalently bound to the $\alpha$-NH$_2$ group of lysine at C-6 position of the L-ascorbic acid and a lysine-proline at C-2 position of the L-ascorbic acid.

The present invention provides a process of producing L-ascorbic acid derivatives, comprising the steps of:
1) treating 6-deoxybromoascorbate with lysine/lysine moieties and proline/proline moieties wherein L-ascorbic acid is covalently bound to the lysine/lysine moieties and proline/proline moieties; and
2) isolating said L-ascorbic acid derivatives;
wherein the 6-deoxyaminoascorbate is covalently bound to the carboxyl group of lysine at C-6 position of the L-ascorbic acid.

The present invention provides a process of producing L-ascorbic acid derivatives, comprising the steps of:
1) treating 6-deoxybromoascorbate with lysine/lysine moieties and proline/proline moieties wherein L-ascorbic acid is covalently bound to the lysine/lysine moieties and proline/proline moieties; and
2) isolating said L-ascorbic acid derivatives;
wherein the 6-deoxyaminoascorbate is covalently bound to the with carboxyl group of polylysine at C-6 position of the L-ascorbic acid.

The present invention provides a process of producing L-ascorbic acid derivatives, comprising the steps of:
1) treating 6-deoxybromoascorbate with lysine/lysine moieties and proline/proline moieties wherein L-ascorbic acid is covalently bound to the lysine/lysine moieties and proline/proline moieties; and
2) isolating said L-ascorbic acid derivatives;
wherein the 6-deoxyaminoascorbate is covalently bound to the carboxyl group of lysine-proline at C-6 position of the L-ascorbic acid.

The present invention provides a process of producing L-ascorbic acid derivatives, comprising the steps of:
1) treating 6-deoxybromoascorbate with lysine/lysine moieties and proline/proline moieties wherein L-ascorbic acid is covalently bound to the lysine/lysine moieties and proline/proline moieties; and
2) isolating said L-ascorbic acid derivatives;
wherein the 6-deoxyaminoascorbate is covalently bound to the carboxyl group of proline at C-6 position of the L-ascorbic acid.

The present invention provides a process of producing L-ascorbic acid derivatives, comprising the steps of:
1) treating 6-deoxybromoascorbate with lysine/lysine moieties and proline/proline moieties wherein L-ascorbic acid is covalently bound to the lysine/lysine moieties and proline/proline moieties; and
2) isolating said L-ascorbic acid derivatives;
wherein the 6-deoxyaminoascorbate is covalently bound to the carboxyl group of polyproline at C-6 position of the L-ascorbic acid.

The present invention provides a pharmaceutical composition comprising L-ascorbic acid derivatives as an effective ingredient, together with a pharmaceutical acceptable carrier.

The present invention provides a pharmaceutical composition comprising L-ascorbic acid derivatives as an effective ingredient, together with a pharmaceutical acceptable carrier, wherein the L-ascorbic acid derivatives are selected from the group consisting of ascorbyl-6-lysine, ascorbyl-2-lysine, ascorbyl-6-polylysine, ascorbyl-2,6-dilysine, ascorbyl-6-polylysine-2-lysine, ascorbyl-6-lysine-2-polylysine, ascorbyl-2,6-polylysine, ascorbyl-6-proline, ascorbyl-2-proline, ascorbyl-6-polyproline, ascorbyl-2-polyproline, ascorbyl-2,6-diproline, ascorbyl-2-proline-6-polyproline, ascorbyl-2-polyproline-6-proline, ascorbyl-2,6-diproline, 6deoxyascrobyllysine, 6-deoxyascorbylproline, 6-deoxyascorbylpolylysine, 6deoxyascorbylpolyproline, 6-deoxyascorbyllysine-2-proline, 6-deoxyascorbylproline-2-lysine, 6-deoxyascorbylpolylysine-2-proline, 6-deoxyascorbylpolyproline-2-lysine, 6-deoxyascorbyllysine-2-polyproline, 6-deoxyascorbylproline-2-polylysine, 6-deoxyascorbate proline-2-lysine-proline, 6-deoxyascorbate-2-proline-lysine, 6-deoxyascorbyllysine, 6-deoxyascorbate-lysine-proline, 6-deoxyascorbyl-lysine-2-proline, 6-deoxyascorbyl-polylysine-2-proline, 6-deoxyascorbyl-lysine-2-polyproline, 6-deoxyascorbyl-lysine-2lysine-proline, 6-deoxyamino ascorbyl-polylysine, 6-deoxyamino ascorbyl-lysine-proline, 6-deoxyamino ascorbylproline, 6-deoxyamino ascorblypolyproline.

The present invention provides a topical composition comprising L-ascorbic acid derivatives, wherein the L-ascorbic acid derivatives are selected from the group consisting of ascorbyl-6-lysine, ascorbyl-2-lysine, ascorbyl-6-polylysine, ascorbyl-2,6-dilysine, ascorbyl-6-polylysine-2-lysine, ascorbyl-6-lysine-2-polylysine, ascorbyl-2,6-polylysine, ascorbyl-6-proline, ascorbyl-2-proline, ascorbyl-6-polyproline, ascorbyl-2-polyproline, ascorbyl-2,6-diproline, ascorbyl-2-proline-6-polyproline, ascorbyl-2-polyproline-6-proline, ascrobyl-2,6-diproline, 6deoxyascrobyllysine, 6-deoxyascorbylproline, 6-deoxyascorbylpolylysine, 6deoxyascorbylpolyproline, 6-deoxyascorbyllysine-2-proline, 6-deoxyascorbylproline-2-lysine, 6-deoxyascrobylpolylysine-2-proline, 6-deoxyascorbylpolyproline-2-lysine, 6-deoxyascorbyllysine-2-polyproline, 6-deoxyascorbylproline-2-polylysine, 6-deoxyascorbate proline-2-lysine-proline, 6-deoxyascorbate-2-proline-lysine, 6-deoxyascorbyllysine, 6-deoxyascorbate-lysine-proline, 6-deoxyascorbyl-lysine-2-proline, 6-deoxyascorbylpolylysine-2-proline, 6-deoxyascorbyl-lysine-2-polyproline, 6-deoxyascorbyl-lysine-2lysine-proline, 6-deoxyamino ascorbyl-polylysine, 6-deoxyamino ascorbyl-lysine-proline, 6-deoxyamino ascorbylproline, 6-deoxyamino ascorblypolyproline.

The present invention provides a method of treating damage to skin comprising applying the topical composition to the skin.

The present invention provides a method of preventing oxidation process comprising the pharmaceutical composition comprising L-ascorbic acid derivatives as an effective ingredient, together with a pharmaceutical acceptable carrier.

The present invention provides a method of preventing oxidation process comprising the pharmaceutical composition comprising L-ascorbic acid derivatives as an effective ingredient, together with a pharmaceutical acceptable carrier, wherein the L-ascorbic acid derivatives are selected from the group consisting of ascorbyl-6-lysine, ascorbyl-2-lysine, ascorbyl-6-polylysine, ascorbyl-2,6-dilysine, ascorbyl-6-polylysine-2-lysine, ascorbyl-6-lysine-2-polylysine, ascorbyl-2,6-polylysine, ascorbyl-6-proline, ascorbyl-2-proline, ascorbyl-6-polyproline, ascorbyl-2-polyproline, ascorbyl-2,6-diproline, ascorbyl-2-proline-6-polyproline, ascorbyl-2-polyproline-6-proline, ascrobyl-2,6-diproline, 6-deoxyascorbyllysine, 6-deoxyascorbylproline, 6-deoxyascorbylpolylysine, 6-deoxyascorbylpolyproline, 6-deoxyascorbyllysine-2-proline, 6-deoxyascorbylproline-2-lysine, 6-deoxyascrobylpolylysine-2-proline, 6-deoxyascorbylpolyproline-2-lysine, 6-deoxyascorbyllysine-2-polyproline, 6-deoxyascorbylproline-2-polylysine, 6-deoxyascorbate proline-2-lysine-proline, 6-deoxyascorbate-2-proline-lysine, 6-deoxyascorbyllysine, 6-deoxyascorbate-lysine-proline, 6-deoxyascorbyl-lysine-2-proline, 6-deoxyascorbylpolylysine-2-proline, 6-deoxyascorbyl-lysine-2-polyproline, 6-deoxyascorbyllysine-2lysine-proline, 6-deoxyamino ascorbyl-polylysine, 6-deoxyamino ascorbyl-lysine-proline, 6-deoxyamino ascorbylproline, 6-deoxyamino ascorblypolyproline.

The present invention provides a method of preventing or retarding aging comprising the pharmaceutical composition comprising L-ascorbic acid derivatives as an, effective ingredient, together with a pharmaceutical acceptable carrier.

The present invention provides a method of preventing or retarding aging comprising the pharmaceutical composition comprising L-ascorbic acid derivatives as an effective ingredient, together with a pharmaceutical acceptable carrier, wherein the L-ascorbic acid derivatives are selected from the group consisting of ascorbyl-6-lysine, ascorbyl-2-lysine, ascorbyl-6-polylysine, ascorbyl-2,6-dilysine, ascorbyl-6-polylysine-2-lysine, ascorbyl-6-lysine-2-polylysine, ascorbyl-2,6-polylysine, ascorbyl-6-proline, ascorbyl-2-proline, ascorbyl-6-polyproline, ascorbyl-2-polyproline, ascorbyl-2,6-diproline, ascorbyl-2-proline-6-polyproline, ascorbyl-2polyproline-6-proline, ascrobyl-2,6-diproline, 6-deoxyascorbyllysine, 6-deoxyascorbylproline, 6-deoxyascorbylpolylysine, 6-deoxyascorbylpolyproline, 6-deoxyascorbyllysine-2-proline, 6-deoxyascorbylproline-2-lysine, 6-deoxyascrobylpolylysine-2-proline, 6-deoxyascorbylpolyproline-2-lysine, 6-deoxyascorbyllysine-2-polyproline, 6-deoxyascorbylproline-2-polylysine, 6-deoxyascorbate proline-2-lysine-proline, 6-deoxyascorbate-2-proline-lysine, 6-deoxyascorbyllysine, 6deoxyascorbate-lysine-proline, 6-deoxyascorbyl-lysine-2-proline, 6-deoxyascorbylpolylysine-2-proline, 6-deoxyascorbyl-lysine-2-polyproline, 6-deoxyascorbyl-lysine-2-lysine-proline, 6-deoxyamino ascorbyl-polylysine, 6-deoxyamino ascorbyl-lysine-proline, 6-deoxyamino ascorbylproline, 6-deoxyamino ascorblypolyproline.

The present invention provides a method of preventive and therapeutic medicine comprising the pharmaceutical composition comprising L-ascorbic acid derivatives as an effective ingredient, together with a pharmaceutical acceptable carrier.

The present invention provides a method of preventive and therapeutic medicine comprising the pharmaceutical composition comprising L-ascorbic acid derivatives as an effective ingredient, together with a pharmaceutical acceptable carrier,wherein the L-ascorbic acid derivatives are selected from the group consisting of ascorbyl-6-lysine, ascorbyl-2-lysine, ascorbyl-6-polylysine, ascorbyl-2,6-dilysine, ascorbyl-6-polylysine-2-lysine, ascorbyl-6-lysine-2-polylysine, ascorbyl-2,6-polylysine, ascorbyl-6-proline, ascorbyl-2-proline, ascorbyl-6-polyproline, ascorbyl-2-polyproline, ascorbyl-2,6-diproline, ascorbyl-2-proline-6-polyproline, ascorbyl-2-polyproline-6-proline, ascrobyl-2,6-diproline, 6-deoxyascorbyllysine, 6-deoxyascorbylproline, 6-deoxyascorbylpolylysine, 6-deoxyascorbylpolyproline, 6-deoxyascorbyllysine-2-proline, 6-deoxyascorbylproline-2-lysine, 6-deoxyascrobylpolylysine-2-proline, 6-deoxyascorbylpolyproline-2-lysine, 6-deoxyascorbyllysine-2-polyproline, 6-deoxyascorbylproline-2-polylysine, 6-deoxyascorbate proline-2-lysine-proline, 6-deoxyascorbate-2-proline-lysine, 6-deoxyascorbyllysine, 6deoxyascorbate-lysine-proline, 6-deoxyascorbyl-lysine-2-proline, 6-deoxyascorbylpolylysine-2-proline, 6-deoxyascorbyl-lysine-2-polyproline, 6-deoxyascorbyl-lysine-2-lysine-proline, 6-deoxyamino ascorbyl-polylysine, 6-deoxyamino ascorbyl-lysine-proline, 6-deoxyamino ascorbylproline, 6-deoxyamino ascorblypolyproline.

The present invention provides a method of stabilizing connective tissue comprising the pharmaceutical composition comprising L-ascorbic acid derivatives as an effective ingredient, together with a pharmaceutical acceptable carrier.

The present invention provides a method of stabilizing connective tissue comprising the pharmaceutical composition comprising L-ascorbic acid derivatives as an effective ingredient, together with a pharmaceutical acceptable carrier, wherein the L-ascorbic acid derivatives are selected from the group consisting of ascorbyl-6-lysine, ascorbyl-2-lysine, ascorbyl-6-polylysine, ascorbyl-2,6-dilysine, ascorbyl-6-polylysine-2-lysine, ascorbyl-6-lysine-2-polylysine, ascorbyl-2,6-polylysine, ascorbyl-6-proline, ascorbyl-2-proline, ascorbyl-6-polyproline, ascorbyl-2-polyproline, ascorbyl-2,6-diproline, ascorbyl-2-proline-6-polyproline, ascorbyl-2-polyproline-6-proline, ascrobyl-2,6-diproline, 6-deoxyascorbyllysine, 6-deoxyascorbylproline, 6-deoxyascorbylpolylysine, 6-deoxyascorbylpolyproline, 6-deoxyascorbyllysine-2-proline, 6-deoxyascorbylproline-2-lysine, 6-deoxyascrobylpolylysine-2-proline, 6-deoxyascorbylpolyproline-2-lysine, 6-deoxyascorbyllysine-2-polyproline, 6-deoxyascorbylproline-2-polylysine, 6-deoxyascorbate proline-2-lysine-proline, 6-deoxyascorbate-2-proline-lysine, 6-deoxyascorbyllysine, 6-deoxyascorbate-lysine-proline, 6-deoxyascorbyl-lysine-2-proline, 6-deoxyascorbyl-polylysine-2-proline, 6-deoxyascorbyl-lysine-2-polyproline, 6-deoxyascorbyl-lysine-2-lysine-proline, 6-deoxyamino ascorbyl-polylysine, 6-deoxyamino ascorbyl-lysine-proline, 6-deoxyamino ascorbylproline, 6-deoxyamino ascorblypolyproline.

The present invention provides a method of preventing the degradation of extracellular matrix comprising the pharmaceutical composition comprising L-ascorbic acid derivatives as an effective ingredient, together with a pharmaceutical acceptable carrier.

The present invention provides a method of preventing the degradation of extracellular matrix comprising the pharmaceutical composition comprising L-ascorbic acid derivatives as an effective ingredient, together with a pharmaceutical acceptable carrier, wherein the L-ascorbic acid derivatives are selected from the group consisting of ascorbyl-6-lysine, ascorbyl-2-lysine, ascorbyl-6-polylysine, ascorbyl-2,6-dilysine, ascorbyl-6-polylysine-2-lysine, ascorbyl-6-lysine-2-polylysine, ascorbyl-2,6-polylysine, ascorbyl-6-proline, ascorbyl-2-proline, ascorbyl-6-polyproline, ascorbyl-2-polyproline, ascorbyl-2,6-diproline, ascorbyl-2-proline-6-polyproline, ascorbyl-2-polyproline-6-proline, ascrobyl-2,6-diproline, 6-deoxyascorbyllysine, 6-deoxyascorbylproline, 6-deoxyascorbylpolylysine, 6-deoxyascorbylpolyproline, 6-deoxyascorbyllysine-2-proline, 6-deoxyascorbylproline-2-lysine, 6-deoxyascrobylpolylysine-2-proline, 6-deoxyascorbylpolyproline-2-lysine, 6-deoxyascorbyllysine-2-polyproline, 6-deoxyascorbylproline-2-polylysine, 6-deoxyascorbate proline-2-lysine-proline, 6-deoxyascorbate-2-proline-lysine, 6-deoxyascorbyllysine, 6-deoxyascorbate-lysine-proline, 6-deoxyascorbyl-lysine-2-proline, 6-deoxyascorbylpolylysine-2-proline, 6-deoxyascorbyl-lysine-2-polyproline, 6-deoxyascorbyl-lysine-2-lysine-proline, 6-deoxyamino ascorbyl-polylysine, 6-deoxyamino ascorbyl-lysine-proline, 6-deoxyamino ascorbylproline, 6-deoxyamino ascorblypolyproline.

The invention is further illustrated but not limited by the following examples.

Figure 1A:
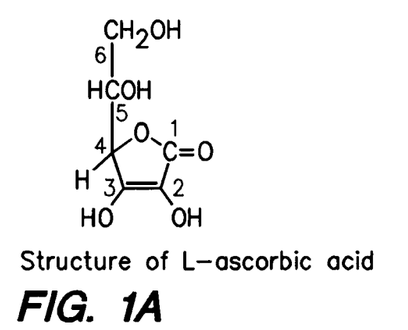
FIGS. 1a, 1b, 1c show the structures of L-ascorbic acid, lysine and proline, respectively.
Figure 1B:
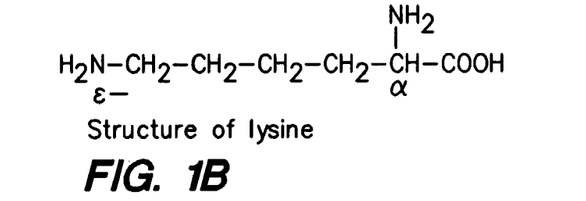
Figure 1C:
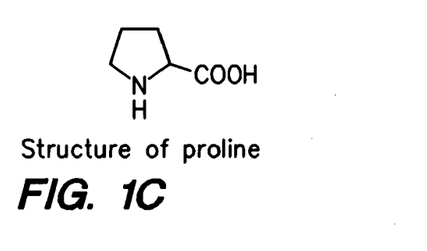
Figure 2:
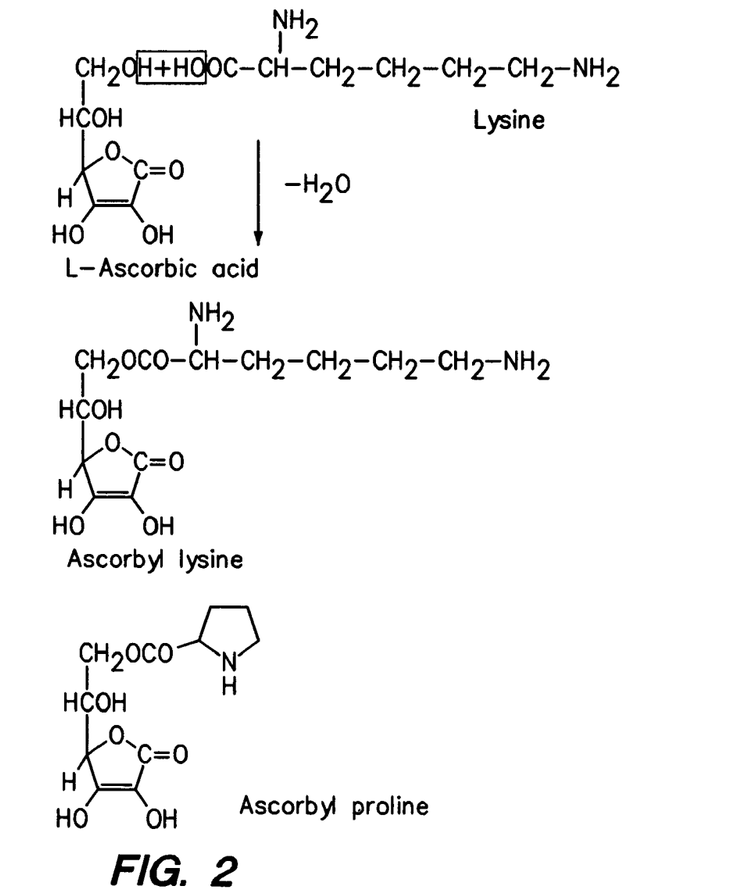
FIG. 2 shows the scheme for the synthesis of ascorbyl lysine and ascorbyl proline.
Figure 3A:
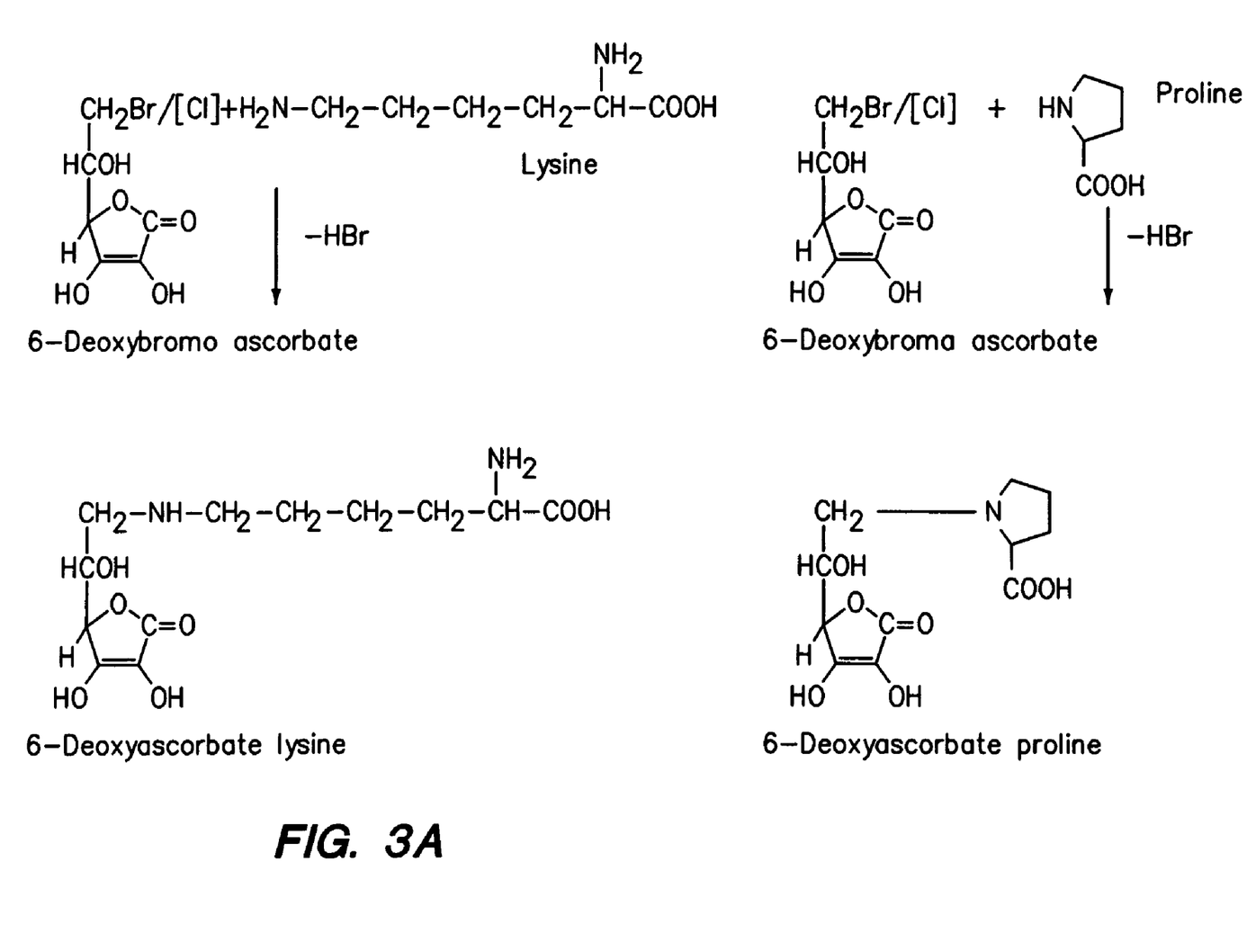
FIG. 3a shows the scheme to synthesize 6-deoxyascorbate lysine. This scheme utilizes the ε-amino group of lysine for binding with 6-deoxybromo ascorbate to produce derivatives linked at 6 position.
Figure 3B:
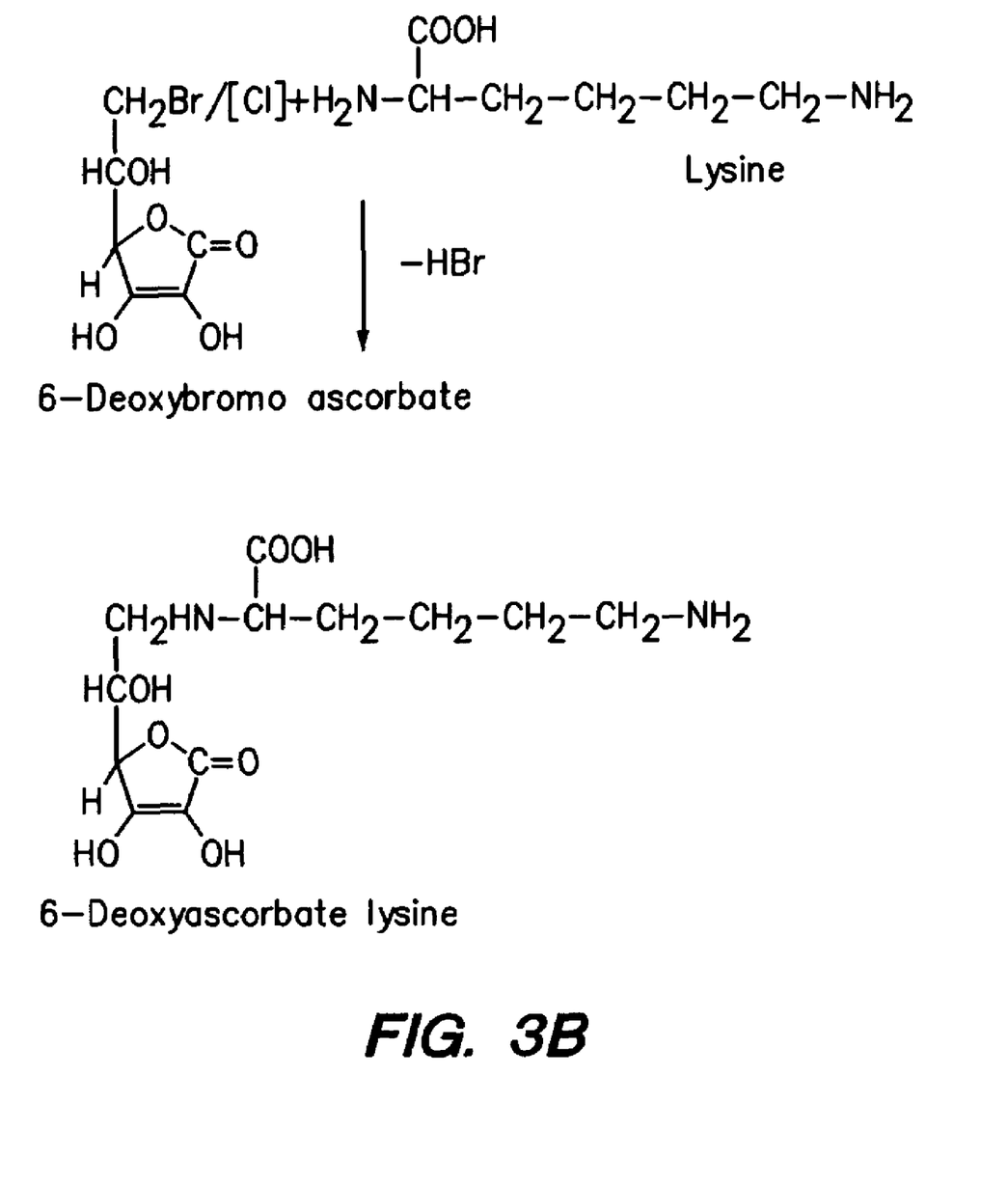
FIG. 3b shows the scheme to synthesize 6-deoxyascorbate lysine utilizing the α-$NH_2$ of lysine and 6-deoxybromoascorbate. The compounds can have an additional substitution at 2-position utilizing the carboxyl group of lysine.
Figure 4:
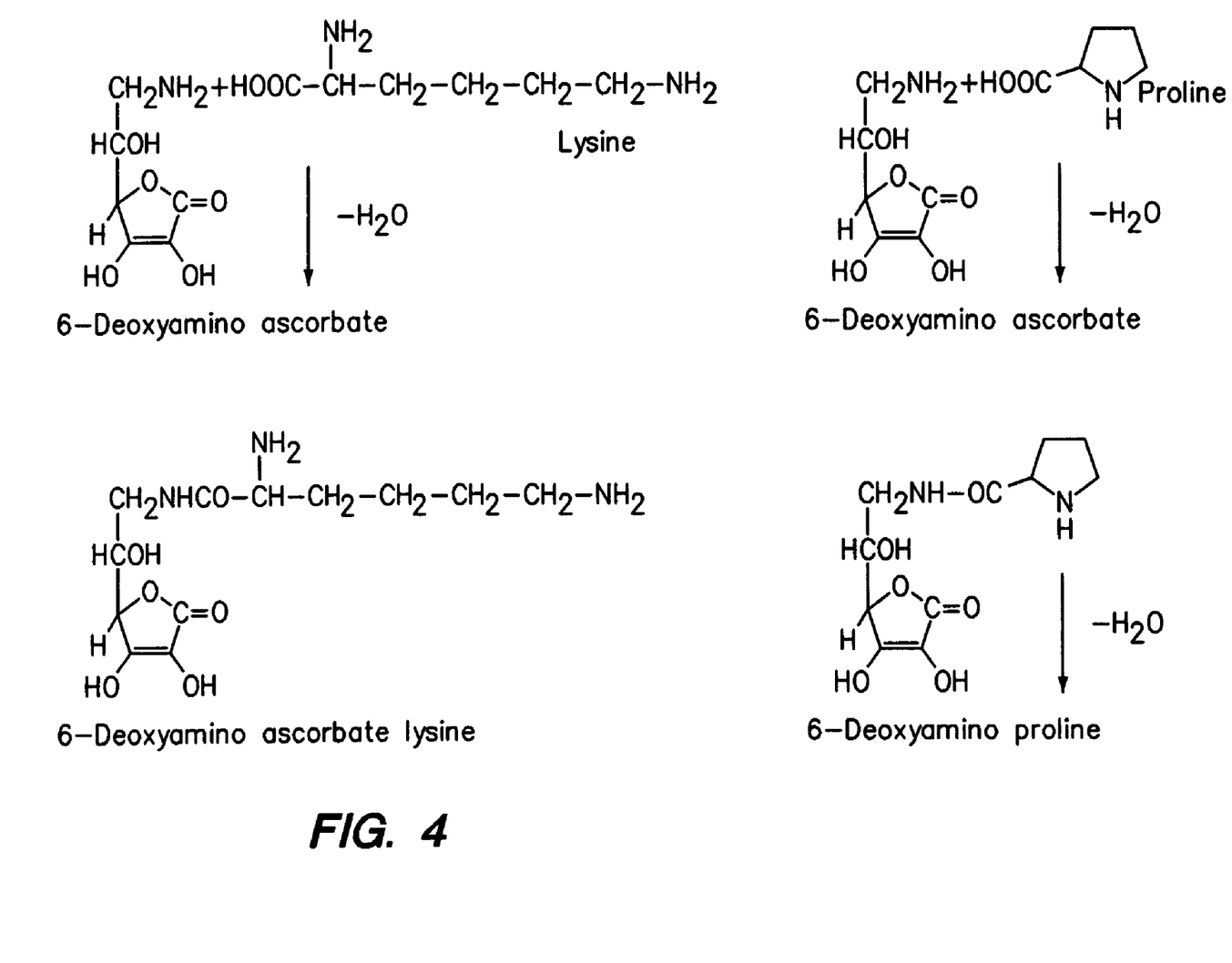
FIG. 4 shows the scheme to synthesize 6-deoxyamino ascorbate and 6-deoxyamino proline utilizing the $NH_2$ group of 6-deoxyamino ascorbate and carboxyl group of proline. The compounds can have an additional substitution at 2-position utilizing the carboxyl group of proline.

The structures of L-Ascorbic acid, L-lysine and L-proline are shown in FIG. 1. These compounds are purchased from Sigma (St. Louis). All other reagents used are of high purity and are obtained either from Sigma or Aldridge Company.

6-Deoxybromcascorbate is synthesized by reacting L-ascorbic acid with hydrogen bromide in acetic acid following the procedure of Block, Lundt and Pedersenj K. Block, I. Lundt and C. Pederson. Carbohydrate Research. 68: 313 (1979))

6-Deoxyamino L-ascorbate is synthesized according to the method of Suskovic (B. Suskovic. Croat Chem Acta. 62: 537 (1989))

C, H and N analysis are performed on all the compounds synthesized and their melting points are determined. NMR, IR, UV and GC/MS are used to establish the structures of the compounds. Purity of the compounds are judged by TLC or HTLC chromatography.

EXAMPLES

Example 1

Synthesis of L-ascorbyl-6-lysine

The standard procedure of condensation of an alcohol with an acid is used. The procedure of Cousins et al R. C. Cousins, P. A. Seib, R. C. Hoseney, C. W. Deyoe, Y. T; Lianc, and D. W. Lillard., J Am Chem Soc: 54, 308 (1977) is detailed as follow.

In brief, ascorbic acid (8 mmoles) is added to a solution of lysine (10 mmoles) in about 20 ml of sulfuric acid. After being stirred for about 2 hours at room temperature, the reaction mixture is allowed to stay at room temperature overnight. It is then poured over crushed ice. Exacted twice with ether and washed with water and dried over sodium sulfate. Ether is removed. The product is crystallized with ethanol and dried in vacuum.

Example 2

Synthesis of L-ascorbyl-6-proline

The procedure is used to synthesized ascorbyl 6-proline. Ascorbic acid (8 mmoles) is, added to a solution of proline (10 mmoles) in about 20 ml of sulfuric acid and stirred for about 2 hours at room temperature and allowed to stay overnight.

The reaction mixture is poured over crushed ice, extracted twice with ether and washed with water. Dried over sodium sulfate, ether is removed and the product is crystallized from ethanol, dried in vacuum.

Example 3

Synthesis of Ascorbyl-2-lysine and Ascorbyl 2-proline

Ascorbyl-2-lysine and ascorbyl-2-proline are also synthesized. To prepare the derivatives at 2-position the hydroxy groups at 5- and 6-positions have to be first protected. Jack and Jones (K. G. A. Jackson and J. K. N. Jones, Can J Chem. 47: 2498 (1969)) procedure is adopted to prepare 5,6-0-isopropylidene ascorbic acid. 5,6-0-isopropylidene ascorbic acid (5 mmoles) in dry pyridine and acetone is added to lysyl chloride (7 mmoles) or prolyl chloride-(7 mmoles) and the products are worked up according to Cousins et al. and crystallized from ethanol.

In additional, 2,6-di-substituted derivatives of lysine or proline are synthesized by reacting L-ascorbic acid either with excess of lysyl chloride or prolyl chloride in dry pyridine as described above.

Furthermore, di-substituted derivatives of L-ascorbic acid with different groups at 2- and 6-positions are synthesized by reacting with respective chlorides by combination of techniques as described above.

Example 4

Synthesis of 6-Deoxyascorbate Lysine

6-Deoxybromo ascorbate (8 mmoles) is reacted with lysine (10 mmoles) in dry pyridine to give the desired product. The α-amino group of lysine is protected so that the ε-group is available for reaction. The reaction is carried out overnight. Pyridine is removed under reduce pressure, poured in ice, extracted with ether, washed with water, dried over sodium sulfate. Ether is removed and crystallized from ethanol.

The other combination of amino acid with ascorbic acid at 2- and 2,6-positions are synthesized by the combination of methods as described above.

6-Deoxyascorbate proline is synthesized by the exact procedure described above for 6-deoxyascorbate lysine. 6-Deoxybromo ascorbate (8 mmoles) is reacted with proline (10 mmoles) in dry pyridine to give 6-deoxyascorbate proline. The product is crystallized form ethanol, dried in vacuum.

The other combination of amino acid with ascorbic acid at 2- and 2,6-positions are synthesized by the combination of method as described above.

Example 6

Synthesis of L-6-deoxyascorbyl Lysine

The ε-group of lysine is protected (7 mmoles) and is reacted with 6-deoxybromo ascorbate (5 mmoles) in dry pyridine to give the said product. After the reaction is over, the product is worked up as described above and crystallized in ethanol.

The compounds with 2-substitution are prepared by the method as described above.

Example 7

Synthesis of 6-Deoxyaminoascorbate Lysine

6-Deoxyamino ascorbate (5 mmoles) is reacted with lysyl chloride (7 mmoles) in dry pyridine and the reaction product is worked up according to Cousine et al. It is crystallized from ethanol.

The other combination of amino acids with ascorbic at 2- and 2,6-positions are prepared as described above.

Example 8

Synthesis of 6-Deoxyaminoascorbate Proline

6-Deoxyamino ascorbate (5 mmoles) is reacted with prolyl chloride (7 mmoles) in dry pyridine and worked up by the method as described above and crystallized from ethanol.

The other combination of amino acid with ascorbic acid at 2- and 2,6-positions are prepared as described above.

6-Deoxyamino ascorbate (5 mmoles) is reacted with prolyl chloride (7 mmoles) in dry pyridine and worked up as described above and crystallized from ethanol. Melting point is determined and C, H and N analysis are performed. Structure is established by NMR, IR, UV and GC/MS methods.

The other combination of amino acid with ascorbic acid at 2- and 2,6-positions are prepared as described above.

The present invention is by no means restricted to these specific embodiments and not to be limited in scope by specific examples described herein. Various modifications of the present invention will become apparent to those skilled in the art from the foregoing description and accompanying figures. Such modifications are intended to fall within the scope of the present invention.

What is claimed is:

1. A method of preparing L-ascorbic acid derivatives, comprising the steps of:
   1) treating 6-deoxybromoascorbate with lysine or lysine moieties wherein L-ascorbic acid is covalently bound to the lysine or lysine moieties; and
   2) isolating the L-ascorbic acid derivatives; wherein the 6-deoxybromoascorbate is covalently bound to one lysine.

2. The method of claim 1 wherein the 6-deoxybromoascorbate is reacted to the .epsilon.-NH.sub.2 group of lysine.

3. A method of preparing L-ascorbic acid derivatives, comprising the steps of:
   1) treating 6-deoxybromoascorbate with lysine or lysine moieties and proline or proline moieties wherein L-ascorbic acid is covalently bound to the lysine or lysine moieties and proline or proline moieties; and
   2) isolating said L-ascorbic acid derivatives.

4. The method of claim 3 wherein the 6-deoxybromoascorbate is covalently bound to a proline at C-2 position of the L-ascorbic acid and one lysine at C-6 position of the L-ascorbic acid.

5. The method of claim 3 wherein the 6-deoxybromoascorbate is covalently bound to the .epsilon.-NH.sub.2 group of lysine.

6. The method of claim 3 wherein the 6-deoxybromoascorbate is covalently bound to a proline and then a lysine-proline at C-2 position of the L-ascorbic acid.

7. The method of claim 3 wherein the 6-deoxybromoascorbate is covalently bound to a proline and then a proline-lysine at C-2 position of the L-ascorbic acid.

8. The method of claim 3 wherein the 6-deoxybromoascorbate is covalently bound to the .alpha.-NH.sub.2 group of lysine.

9. The method of claim 3 wherein the 6-deoxybromoascorbate is covalently bound to lysine-proline.

10. The method of claim 3 wherein the 6-deoxybromoascorbate is covalently bound to the .alpha.-NH.sub.2 group of lysine at C-6 position of the L-ascorbic acid and one proline at C-2 position of the L-ascorbic acid.

11. The method of claim 3 wherein the 6-deoxybromoascorbate is covalently bound to the .alpha.-NH.sub.2 group of lysine at C-6 position of the L-ascorbic acid and a lysine-proline at C-2 position of the L-ascorbic acid.

12. The method of claim 3 wherein the 6-deoxyaminoascorbate is covalently bound to the carboxyl group of lysine at C-6 position of the L-ascorbic acid.

13. The method of claim 3 wherein the 6-deoxyaminoascorbate is covalently bound to the carboxyl group of lysine-proline at C-6 position of the L-ascorbic acid.

14. The method of claim 3 wherein the 6-deoxyaminoascorbate is covalently bound to the carboxyl group of proline at C-6 position of the L-ascorbic acid.

15. A method of producing L-ascorbic acid derivatives, comprising the steps of:
   1) treating 6-deoxybromoascorbate with lysine/lysine moieties and proline/proline moieties wherein L-ascorbic acid is covalently bound to the lysine/lysine moieties and proline/proline moieties; and
   2) isolating said L-ascorbic acid derivatives; wherein the 6-deoxyaminoascorbate is covalently bound to the carboxyl group of polyproline at C-6 position of the L-ascorbic acid.

* * * * *